(12) United States Patent
Saburi et al.

(10) Patent No.: US 11,813,088 B2
(45) Date of Patent: Nov. 14, 2023

(54) GRIP

(71) Applicant: TOYODA GOSEI CO., LTD., Kiyosu (JP)

(72) Inventors: Chikara Saburi, Kiyosu (JP); Rie Ono, Kiyosu (JP); Takamitsu Murai, Kiyosu (JP); Tatsuya Nobunaga, Nagakute (JP); Kentaro Mizuno, Nagakute (JP)

(73) Assignee: TOYODA GOSEI CO., LTD., Aichi-pref. (JP)

( * ) Notice: Subject to any disclaimer, the term of this patent is extended or adjusted under 35 U.S.C. 154(b) by 841 days.

(21) Appl. No.: 16/884,248

(22) Filed: May 27, 2020

(65) Prior Publication Data

US 2020/0377138 A1 Dec. 3, 2020

(30) Foreign Application Priority Data

May 29, 2019 (JP) .................................. 2019-99991

(51) Int. Cl.
*A61B 5/00* (2006.01)
*B62D 1/04* (2006.01)
*B62D 1/06* (2006.01)
*A61B 5/318* (2021.01)

(52) U.S. Cl.
CPC ............ *A61B 5/6893* (2013.01); *A61B 5/318* (2021.01); *B62D 1/046* (2013.01); *B62D 1/06* (2013.01)

(58) Field of Classification Search
CPC ... A61B 5/6893; A61B 5/0402; A61B 5/0425; A61B 5/318; A61B 5/332; A61B 2560/0468; B62D 1/046; B62D 1/06
See application file for complete search history.

(56) References Cited

U.S. PATENT DOCUMENTS 8,171,820 B2 * 5/2012 Song .................... B62D 1/046
340/576
2011/0048163 A1 3/2011 Song

FOREIGN PATENT DOCUMENTS

JP 2011-50727 A 3/2011

* cited by examiner

*Primary Examiner* — Jeremy R Severson
(74) *Attorney, Agent, or Firm* — POSZ LAW GROUP, PLC

(57) ABSTRACT

A grip includes a core that forms a structure of the grip and has electrical conductivity, a sensing electrode for detecting a biological signal of a user, and a ground electrode that is connected with a reference voltage portion. The core, the sensing electrode and the ground electrode are insulated from one another. The core is disposed inside the grip, and the sensing electrode is exposed on a surface of the grip. The sensing electrode and the core are connected with one another via a voltage follower circuit. The ground electrode is located at such a position that the core is able to reduce a parasitic capacitance which would be formed between the ground electrode and the sensing electrode.

11 Claims, 7 Drawing Sheets

GRIP

CROSS REFERENCE TO RELATED APPLICATIONS

The present application claims priority from Japanese Patent Application No. 2019-099991 of Nobunaga et al., filed on May 29, 2019, the entire disclosure of which is incorporated herein by reference.

BACKGROUND

1. Technical Field

The present disclosure relates to a grip that is able to monitor a biological signal of a user.

2. Description of Related Art

JP 2011-050727 A discloses a steering wheel (i.e. grip) for a vehicle that is able to monitor a biological signal of a driver such as an electrocardiogram (ECG).

A biological signal is weaker in strength than noises (e.g. static electricity, hum) that are superimposed on it. That is, a measurement of a biological signal has a low S/N ratio (signal-to-noise ratio). The steering wheel (i.e. grip) of the above-mentioned patent literature is not provided with any structures for improving the S/N ratio at measuring of the biological signal. Therefore, it would be difficult for the steering wheel of the above-mentioned patent literature to detect the biological signal.

SUMMARY

An exemplary embodiment of the invention relates to a grip that includes a core which forms a structure of the grip and has electrical conductivity, a sensing electrode for detecting a biological signal of a user, and a ground electrode that is connected with a reference voltage portion. The core, the sensing electrode and the ground electrode are insulated from one another. The core is disposed inside the grip, and the sensing electrode is exposed on a surface of the grip. The sensing electrode and the core are connected with one another via a voltage follower circuit. The ground electrode is located at such a position that the core is able to reduce a parasitic capacitance which exists between the ground electrode and the sensing electrode.

DETAILED DESCRIPTION

First Embodiment

Configuration of a Steering Wheel 1

Figure 1:
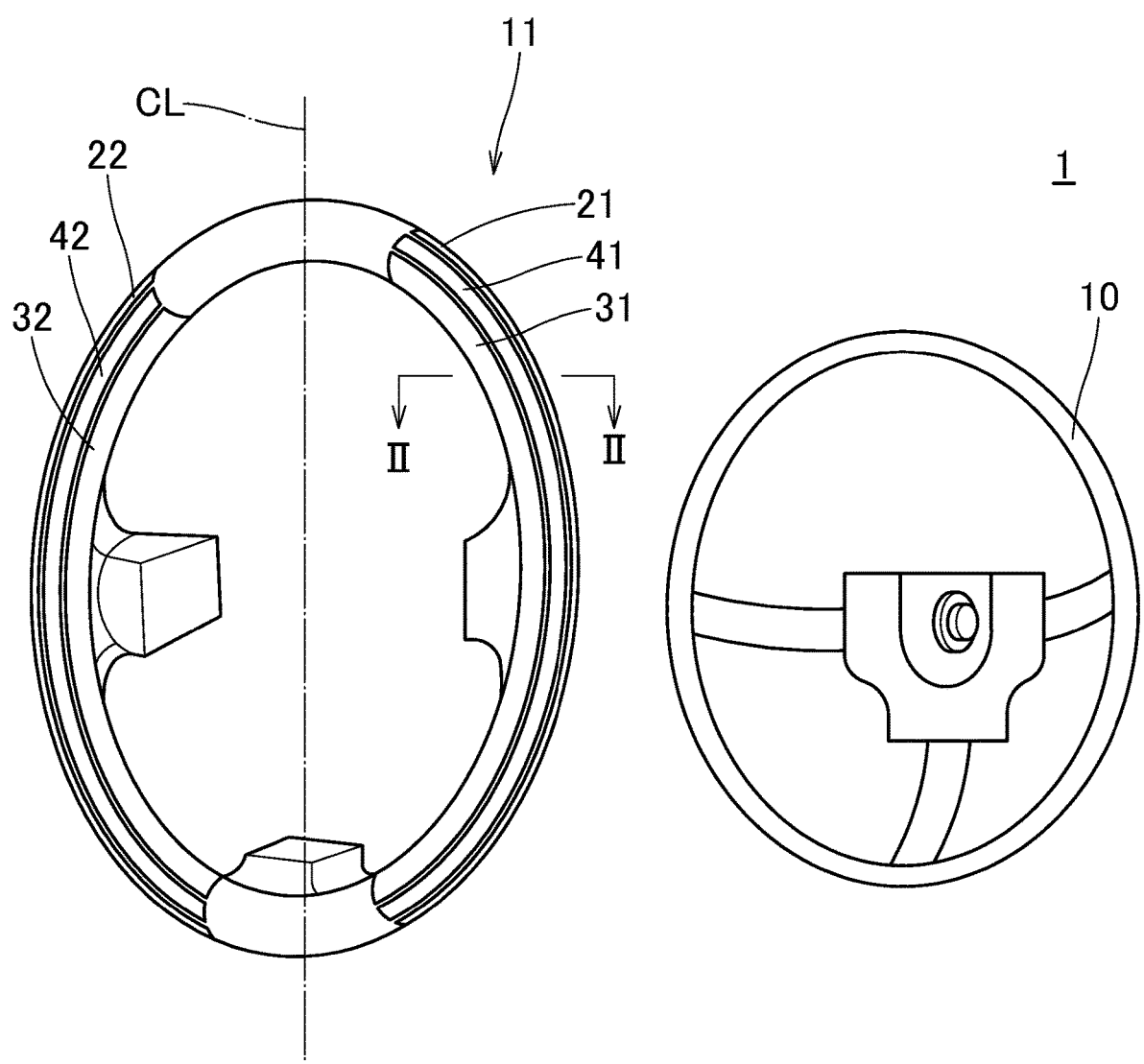
FIG. 1 is an exploded perspective view of a steering wheel 1 in accordance with a first embodiment.

FIG. 1 is an exploded perspective view of a steering wheel in accordance with a first embodiment. The steering wheel 1 as a grip includes a core 10 that forms a structure of the steering wheel, and a cladding layer 11 that is mounted around the core 10. The core 10 is formed from a material having electrical conductivity. The material of the core 10 may contain iron, aluminum, magnesium or the like. The cladding layer 11 is a structure having an insulating property. The cladding layer 11 is, by way of example, formed from synthetic resin by in-mold technology.

A line passing through the center of an annular rim in an up and down direction in the steering wheel 1 as steered straight ahead is defined here as a center line CL. A sensing electrode 21, a ground electrode 31, and at least one shield electrode 41 (two shield electrodes 41 are provided in this specific embodiment) are disposed on the right side of the center line CL. These are the electrodes for the right hand for conducting a measurement using the right hand of a user. A sensing electrode 22, a ground electrode 32, and at least one shield electrode 42 (two shield electrodes 42 are provided in this specific embodiment) are disposed on the left side of the center line CL. These are the electrodes for the left hand for conducting a measurement using the left hand of the user. The electrodes for the right hand have the same structures as the electrodes for the left hand. Therefore, the electrodes for the right hand (i.e. the sensing electrode 21, the ground electrode 31, and the shield electrode 41) will be described hereinafter in detail.

Figure 2:
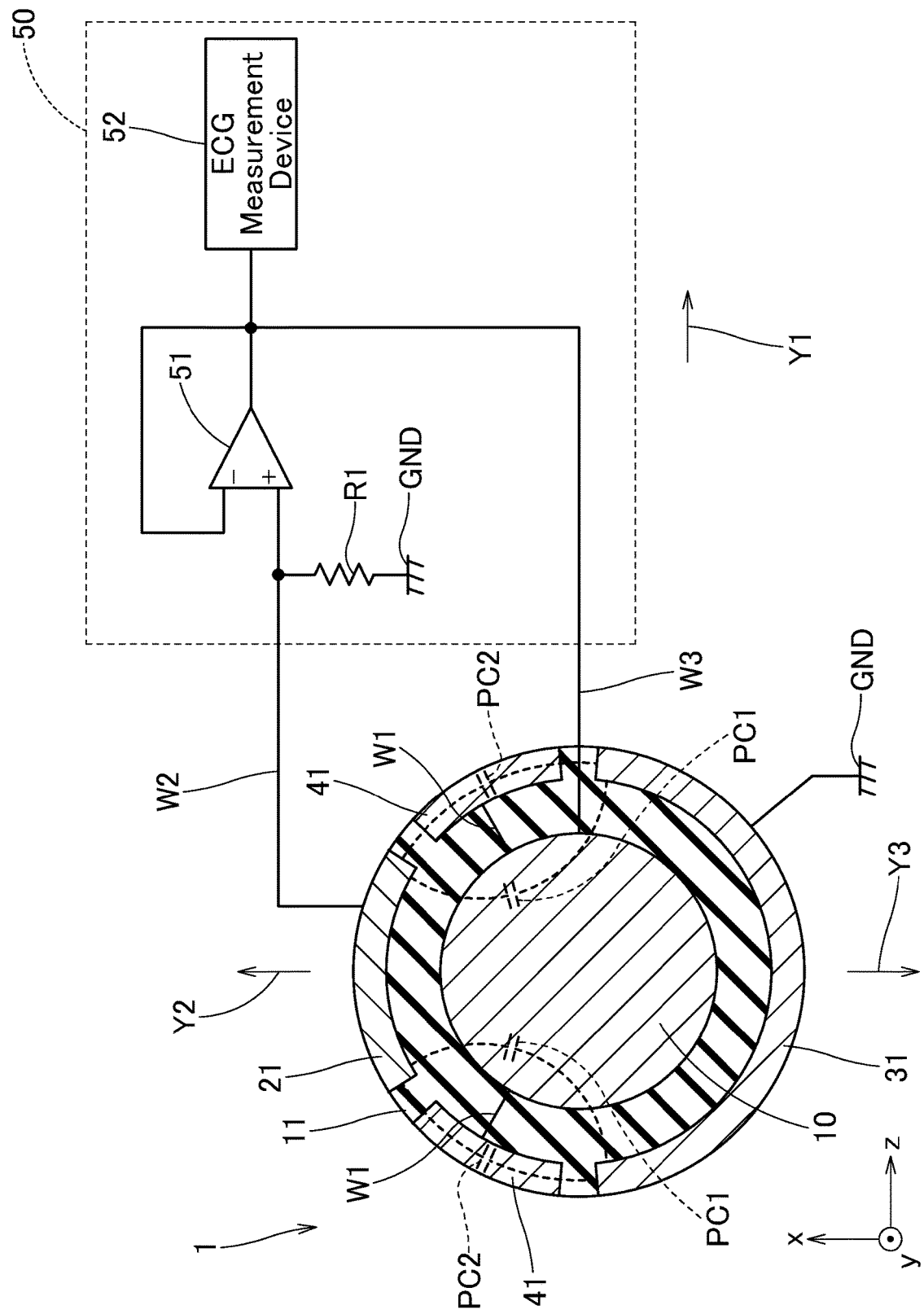
FIG. 2 is a cross-sectional view of the steering wheel 1 taken along line II-II of FIG. 1.

FIG. 2 is a cross-sectional view of the rim of the steering wheel 1 as the grip taken along line II-II of FIG. 1. In FIG. 2, an arrow Y1 points towards a front side of the user, an arrow Y2 points towards an outer peripheral side of the steering wheel 1, and an arrow Y3 points towards a center of the steering wheel 1. The core 10 is disposed proximate to the center of the cross-sectional surface. The sensing electrode 21, ground electrode 31, and shield electrodes 41 are exposed on the surface of the cladding layer 11 (i.e. on the surface of the grip). The sensing electrode 21, ground electrode 31, and shield electrodes 41 are insulated from one another by the cladding layer 11. Each of the sensing electrode 21, ground electrode 31, and shield electrodes 41 is a dry electrode.

The sensing electrode 21 detects an electrocardiogram (ECG), i.e. a biological signal, of the driver. The sensing electrode 21 is located on the outer circumference of the cross-sectional surface. The ground electrode 31 is connected with a body ground GND which serves as a reference voltage portion. The ground electrode 31 is provided to give a reference potential to a human body. The ground electrode 31 is located separate from the sensing electrode 21 on the outer circumference of the cross-sectional surface. The position of the ground electrode 31 is determined such that the core 10 would be able to reduce a parasitic capacitance which exists between the ground electrode 31 and the sensing electrode 21. The position of the ground electrode 31 will be described in detail below. The shield electrodes 41 are each electrically connected with the core 10 by a wire W1. The shield electrodes 41 are located between the sensing electrode 21 and the ground electrode 31 on the outer circumference of the cross-sectional surface.

The steering wheel 1 is connected with a measurement system 50. As can be seen in FIG. 2, the measurement system 50 includes an operational amplifier 51, a resistor R1, and an ECG measurement device 52. The sensing electrode 21 is connected with a non-inverting input terminal of the operational amplifier 51 by a wire W2. The non-inverting input terminal is connected with the body ground GND via the resistor R1. An output terminal of the operational amplifier 51 is connected with an inverting input terminal of the operational amplifier 51. This way the operational amplifier 51 functions as a voltage follower circuit. The output terminal of the operational amplifier 51 is connected with the ECG measurement device 52, and is also connected with the core 10 by a wire W3. That is, due to the mutual connection via the voltage follower circuit, the sensing electrode 21 and the core 10 are at the same potential.

The ECG measurement device 52 acquires a differential signal between the sensing electrode 21 for the right hand and the sensing electrode 22 for the left hand as an electrocardiogram. More particularly, the ECG measurement device 52 measures a change in electric potential caused by capacitive coupling occurring between a palm of the user and either one of the sensing electrode 21 and sensing electrode 22 relative to a voltage measured by the other electrode as a reference potential. A known circuit structure can be used for the ECG measurement device 52. Therefore, a detailed description of the ECG measurement device 52 is omitted.

First Objective with Respect to Measurement of Electrocardiogram

Figure 3:
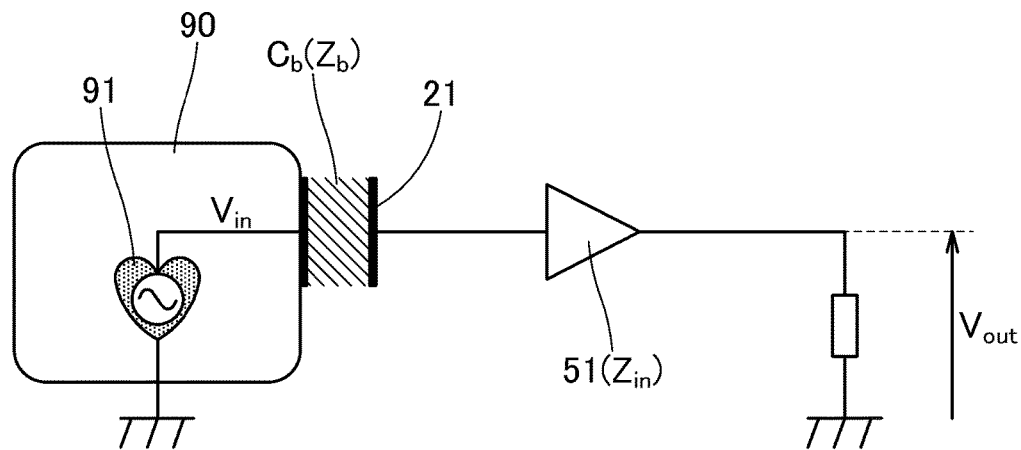
FIG. 3 is a model of a measurement system of electrocardiogram.

FIG. 3 is a model of a measurement system of electrocardiogram in accordance with the first embodiment. In this measurement system, a relationship between a voltage change Vin of a heart 91 and an output voltage $V_{out}$ of the operational amplifier 51 is expressed by the following mathematical formula:

$$V_{out} = \frac{Z_{in}}{\frac{1}{j\omega C_b} + Z_{in}} \cdot V_{in} = \frac{Z_{in}}{Z_b + Z_{in}} \cdot V_{in}$$

where $C_b$ is a capacitive coupling between the palm of the sitter 90 and the sensing electrode 21, $Z_b$ is an impedance which includes an electrode impedance $Z_e$ in connection with the sensing electrode 21 and a body impedance $Z_{skin}$ of the skin of the palm, the impedance $Z_b$ can be expressed as "$1/j\omega C_b$", and $Z_{in}$ is an input impedance of the operational amplifier 51.

The above mathematical formula shows that the output voltage $V_{out}$ depends on a voltage ratio of the input impedance $Z_{in}$ to the impedance $Z_b$. That is, in order to increase a sensitivity in acquisition of an electrocardiogram, it is necessary to increase the input impedance $Z_{in}$ of the operational amplifier 51.

Here, the sensing electrode 21 used in the steering wheel 1 of the first embodiment is a dry electrode. Conductive gel is not applied to a dry electrode, unlike in a case of a wet electrode. Accordingly, a dry electrode has a higher impedance than a wet electrode because it has a not so good connection with the skin as the wet electrode. This increases the impedance $Z_b$. The first objective is to increase the input impedance $Z_{in}$ in order to increase the output voltage $V_{out}$.

Second Objective with Respect to Measurement of Electrocardiogram

Figure 4:
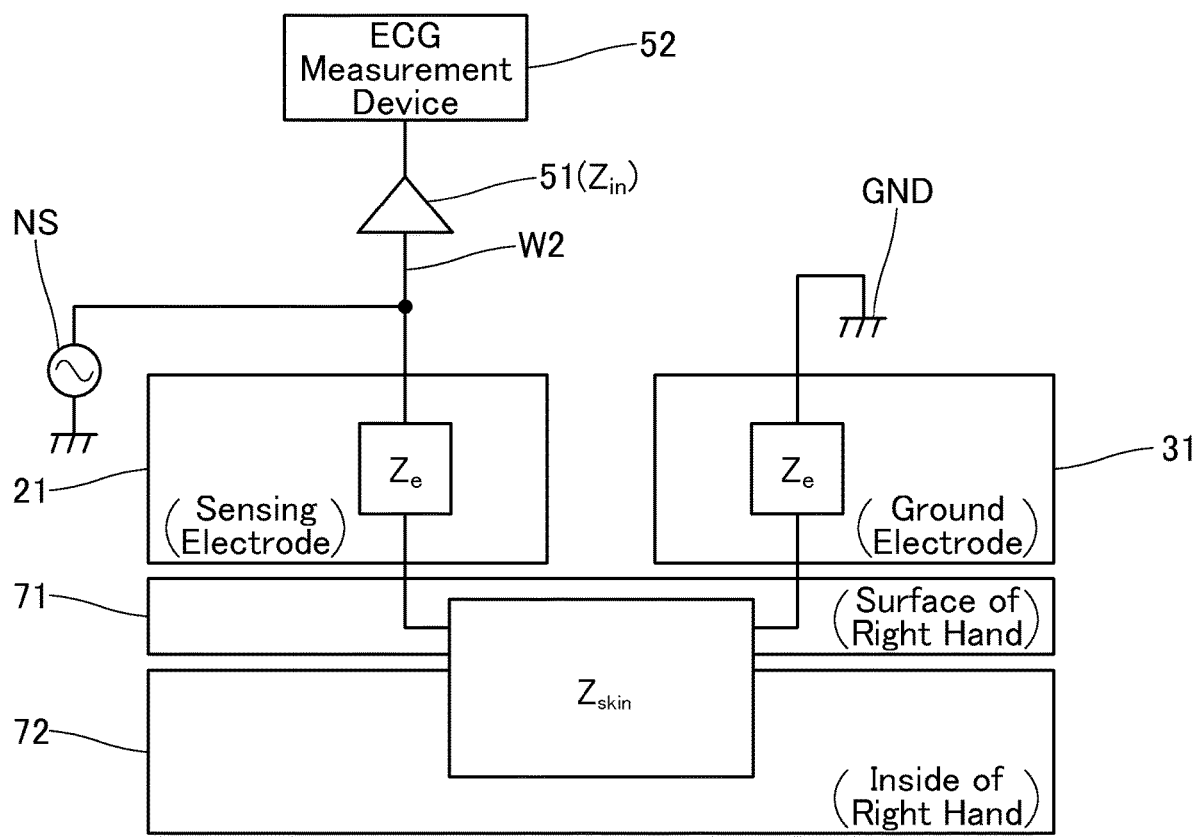
FIG. 4 is a model that represents a superimposition of a noise on a detected signal.

FIG. 4 is a model that illustrates a superimposition of a noise (such as static electricity and hum) on a detected signal at the time when a surface 71 of the right hand of a user is in contact with the sensing electrode 21 and the ground electrode 31. The electrode impedance $Z_e$ is an impedance pertaining to each of the sensing electrode 21 and ground electrode 31. The body impedance $Z_{skin}$ is an impedance pertaining to the surface 71 of the right hand and an inside 72 of the right hand (such as body fluid). The input impedance $Z_{in}$ is an impedance of the operational amplifier 51. Here, a noise source NS is supposed to exist on a pathway of the wire W2. When $A_n$ is a noise current which enters into the detected signal, a noise voltage $V_n$ fed into the operational amplifier 51 is expressed by a formula (1) shown below:

$$V_n = \frac{Z_{in}(2Z_e + Z_{skin})}{Z_{in} + 2Z_e + Z_{skin}} A_n \quad (1)$$

Here, the input impedance $Z_{in}$ is ten to the twelfth power in order of magnitude, the body impedance $Z_{skin}$ is ten to the sixth power in order of magnitude, and the electrode impedance $Z_e$ is ten to the fourth power in order of magnitude. Since the input impedance $Z_{in}$ is sufficiently larger than the body impedance $Z_{skin}$ and the electrode impedance $Z_e$, the formula (1) can be approximated by a formula (2) shown below:

$$V_n = (2Z_e + Z_{skin})A_n \quad (2)$$

The formula (2) shows that the noise voltage $V_n$ is proportional to an impedance of a pathway from the entry point of the noise emitted from the noise source NS to the body ground GND. Since a value of the body impedance $Z_{skin}$ is high, the noise voltage $V_n$ is high. Since an electrocardiographic signal, the object of measurement, is smaller than the noise voltage $V_n$ which is superimposed thereon, the S/N ratio of the measurement of electrocardiogram is low. Therefore, it is a second objective to build an electrode structure that would reduce the superimposition of the noise. A value of the noise voltage $V_n$ varies depending on various parameters such as a portion of the human body which the electrode contacts with and a distance to the body ground GND.

Electrode Structure that Achieves the Objectives

Figure 5:
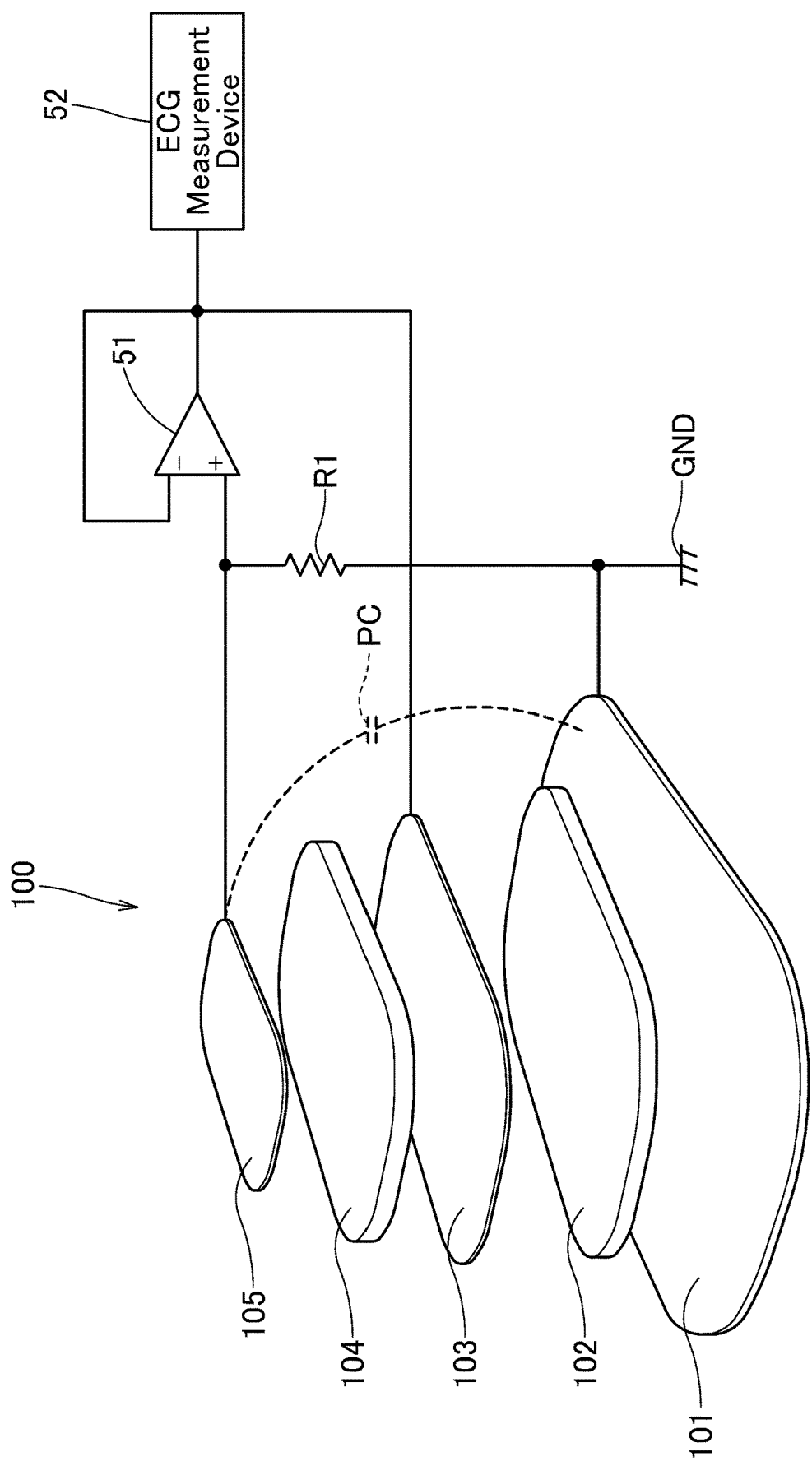
FIG. 5 depicts an electrode structure 100.

An electrode structure 100 depicted in FIG. 5 is presented as an example of the electrode structure that is able to achieve the first and second objectives described above. Members with common reference numerals with FIG. 2 have the same configurations as FIG. 2, therefore detailed descriptions of those members will be omitted. The electrode structure 100 has a five-layer structure. More specifically, the electrode structure 100 has a structure in which a ground electrode 101, a first insulating layer 102, a shield electrode 103, a second insulating layer 104, and a sensing electrode 105 are stacked in sequence. The sensing electrode 105, the shield electrode 103, and the ground electrode 101 are insulated from one another by the first insulating layer 102 and second insulating layer 104. Although FIG. 5 depicts the layers as exploded for the illustrative purpose, the layers are actually in close contact with one another.

The sensing electrode 105 is connected with the non-inverting input terminal of the operational amplifier 51. The non-inverting input terminal is connected with the body ground GND via a resistor R1. The output terminal of the operational amplifier 51 is connected with the inverting input terminal. The output terminal of the operational amplifier 51 is also connected with the ECG measurement device 52, and with the shield electrode 103.

The sensing electrode 105 detects an electrocardiogram (ECG) of the driver. The ground electrode 101 prevents a noise from entering into the sensing electrode 105 from outside. The shield electrode 103 and the sensing electrode 105 are at the same potential since the shield electrode 103 is connected with the sensing electrode 105 via the operational amplifier 51 (i.e. a voltage follower circuit). The shield electrode 103 is located between the ground electrode 101 and the sensing electrode 105.

As discussed in the section of "FIRST OBJECTIVE", the first objective is to increase the input impedance $Z_{in}$ of the operational amplifier 51. The shield electrode 103 prevents a parasitic capacitance PC from being formed between the sensing electrode 105 and ground electrode 101, which parasitic capacitance would otherwise act to decrease the input impedance $Z_{in}$. That is, the shield electrode 103 prevents the input impedance $Z_{in}$ from dropping.

As discussed in the section of "SECOND OBJECTIVE", the second objective is to suppress a superimposition of a noise voltage $V_n$ on a detected signal. The shield electrode 103 exerts a function that prevents a noise from entering into the sensing electrode 105 from the outside noise source. That is, the ground electrode 101 and the shield electrode 103 build in combination a double shield for preventing noise contamination. Thus, the noise voltage $V_n$ is suppressed.

Effects Exerted by the Steering Wheel 1

The electrode structure 100 described above and shown in FIG. 5 cannot be mounted on a steering wheel (i.e. grip) as it is because it has the complicated five-layer structure and the steering wheel has a limited space. In the steering wheel 1 in accordance with the first embodiment, as shown in FIG. 2, the sensing electrode 21 and the core 10 are connected with one another via the operational amplifier 51 (i.e. voltage follower circuit), thus at the same potential. Further, in the cross-sectional surface of the rim of the steering wheel (i.e. grip) 1, the ground electrode 31 and the sensing electrode 21 are located across the core 10 which is disposed at the center of the cross-sectional surface of the rim. This way the core 10 serves as the shield electrode 103 in the five-layer electrode structure 100 depicted in FIG. 5. That is, in the steering wheel 1, the ground electrode 31, the cladding layer (or insulating layer) 11, the core 10, the cladding layer 11, and the sensing electrode 21 form the five-layer structure, as shown in FIG. 2. That is, the electrode structure 100 depicted in FIG. 5 is successfully mounted on the steering wheel by simplification and space-conserving design of the electrode structure. As a consequence, the core 10 helps prevent a parasitic capacitance PC1 (FIG. 2), which is a capacitance formed inside the steering wheel 1, from being formed between the ground electrode 31 and sensing electrode 21, thus suppressing a dropping of the input impedance $Z_{in}$ of the operational amplifier 51. Moreover, a noise contamination is prevented due to the double shield formed by the ground electrode 31 and the core 10.

A parasitic capacitance PC2 (FIG. 2) which may be formed in a vicinity of the surface of the rim of the steering wheel 1 (i.e. grip) and between the ground electrode 31 and sensing electrode 21 can also be a cause of dropping of the input impedance $Z_{in}$ of the operational amplifier 51. In the steering wheel 1 in accordance with the first embodiment, as shown in FIG. 2, the shield electrode 41 is located on the surface of the steering wheel 1 between the ground electrode 31 and sensing electrode 21. Since the shield electrode 41 and the core 10 are at the same potential, the shield electrode 41 exerts the same function as the core 10. That is, the shield electrode 41 helps prevent the parasitic capacitance PC2 from being formed, and suppress the dropping of the input impedance $Z_{in}$ of the operational amplifier 51.

It is a first key factor for enhancing a noise resistance of measurement of an electrocardiogram that the human body is brought into firm contact with the ground electrode, because the noise voltage $V_n$ is proportional to the impedance of the pathway (from the entry point of the noise) to the body ground GND, as explained above in connection with FIG. 4. If the electrode impedance $Z_e$ rises due to an insufficient contact with the ground electrode 31, the noise voltage $V_n$ rises as well, as can be understood from the formula (2). It is a second key factor for enhancement of the noise resistance that a distance between the sensing electrode and ground electrode is short and the human body is brought into contact with the sensing electrode and the ground electrode at the same time, because the body impedance $Z_{skin}$ shown in FIG. 4 depends on the distance (between the sensing electrode and the ground electrode). Addressing these issues, in the art described in the first embodiment, the ground electrode 31 is exposed on the surface of the steering wheel (i.e. grip) as can be seen in FIG. 2. With this, the palm of the user is naturally brought into contact with the ground electrode 31 when he/she grips the steering wheel. Further, the sensing electrode 21 and the ground electrode 31 are located in proximity to one another on the outer circumference of the cross-sectional surface of the steering wheel 1. With this, the palm is brought into contact with the sensing electrode 21 and ground electrode 31 at the same time. As a consequence, the first and second key factors mentioned above are fulfilled, so that the noise resistance is enhanced.

Second Embodiment

Figure 6:
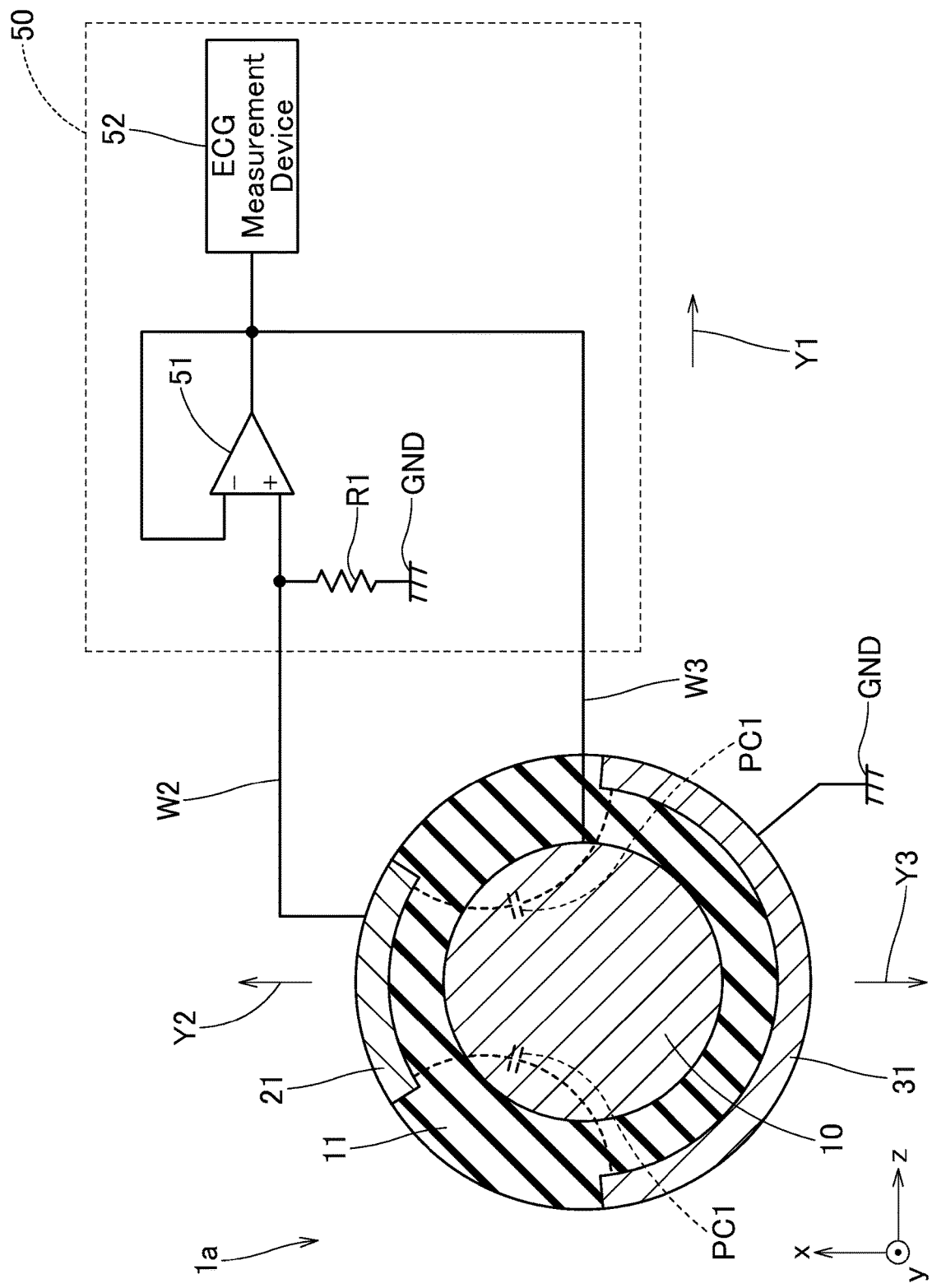
FIG. 6 is a cross-sectional view of a steering wheel 1a in accordance with a second embodiment.

FIG. 6 is a cross-sectional view of a rim of a steering wheel (i.e. grip) 1a in accordance with the second embodiment. Members with common reference numerals with the steering wheel 1 of the first embodiment have the same configurations as the first embodiment, therefore detailed descriptions of those members will be omitted. Compared with the steering wheel 1 of FIG. 2, the steering wheel 1a shown in FIG. 6 does not include any shield electrodes 41. With no shield electrode 41, the parasitic capacitance PC2 cannot be reduced, and the input impedance of the operational amplifier cannot be prevented from dropping. Still the core 10 is able to prevent the parasitic capacitance PC1 (the capacitance formed inside the steering wheel 1a) from being formed. The steering wheel 1a of FIG. 6 has an even simpler structure than the steering wheel 1 of FIG. 2, thus, is conducive to cost reduction.

Third Embodiment

Figure 7:
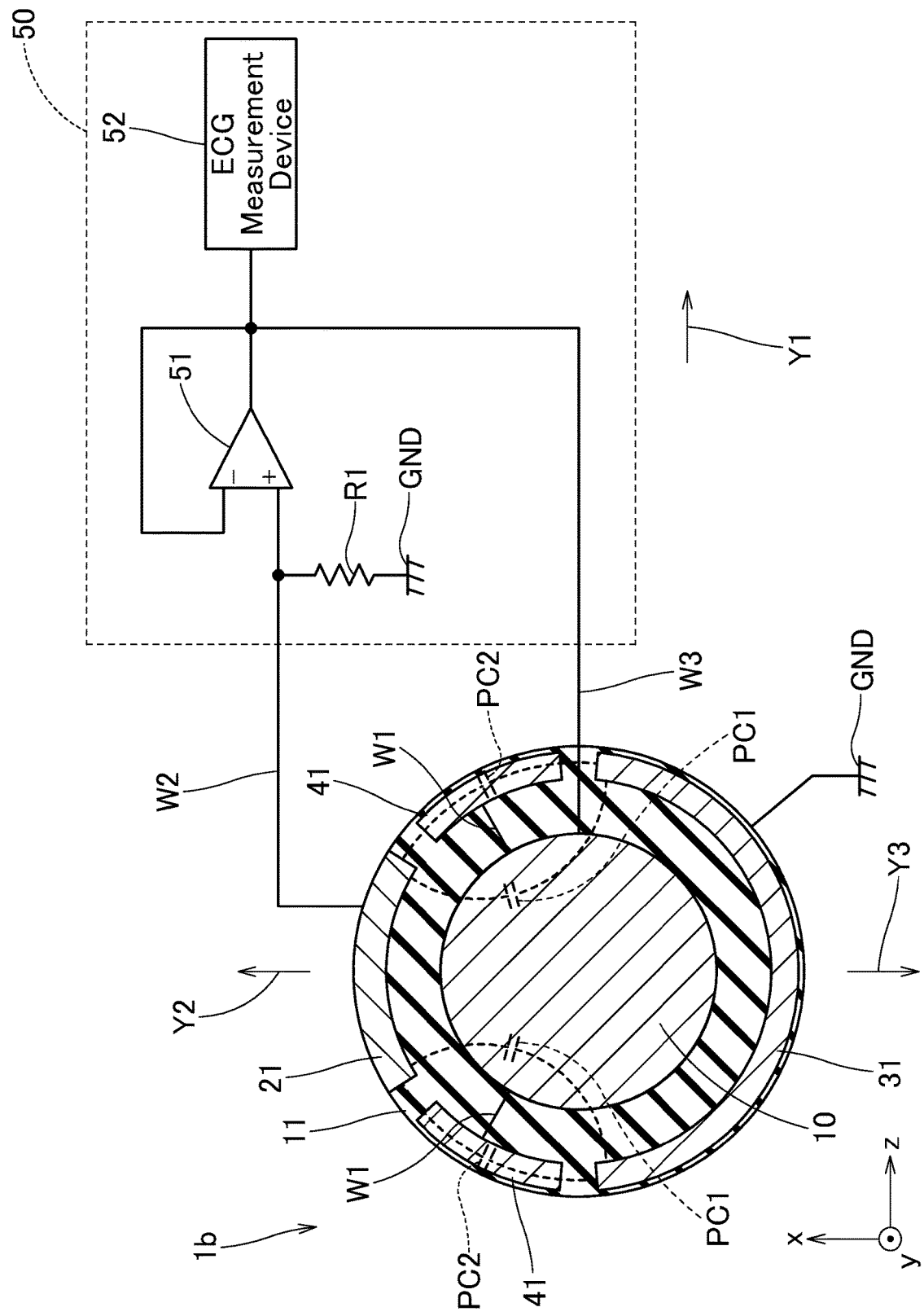
FIG. 7 is a cross-sectional view of a steering wheel 1b in accordance with a third embodiment.

FIG. 7 is a cross-sectional view of a rim of a steering wheel (i.e. grip) 1b in accordance with the third embodiment. Members with common reference numerals with the steering wheel 1 of the first embodiment have the same configurations as the first embodiment, therefore detailed descriptions of those members will be omitted. The steering wheel 1b of FIG. 7 is different from the steering wheel 1 of FIG. 2 in that the ground electrode 31 and the shield electrodes 41 are located in a vicinity of the outer circumference of the cross-sectional surface of the grip but are not exposed on the surface of the grip. With this configuration, since the ground electrode 31 cannot be brought into firm contact with the palm, the noise resistance of measurement of electrocardiogram cannot be enhanced. Nevertheless the core 10 is able to prevent the parasitic capacitance PC1 from being formed with this configuration. Further, the shield electrodes 41 prevent the parasitic capacitance PC2 from being formed. Moreover, a less exposure of the electrodes on the surface of the steering wheel 1 will increase a degree of freedom of design and improve a grip performance of the steering wheel.

Fourth Embodiment

Figure 8:
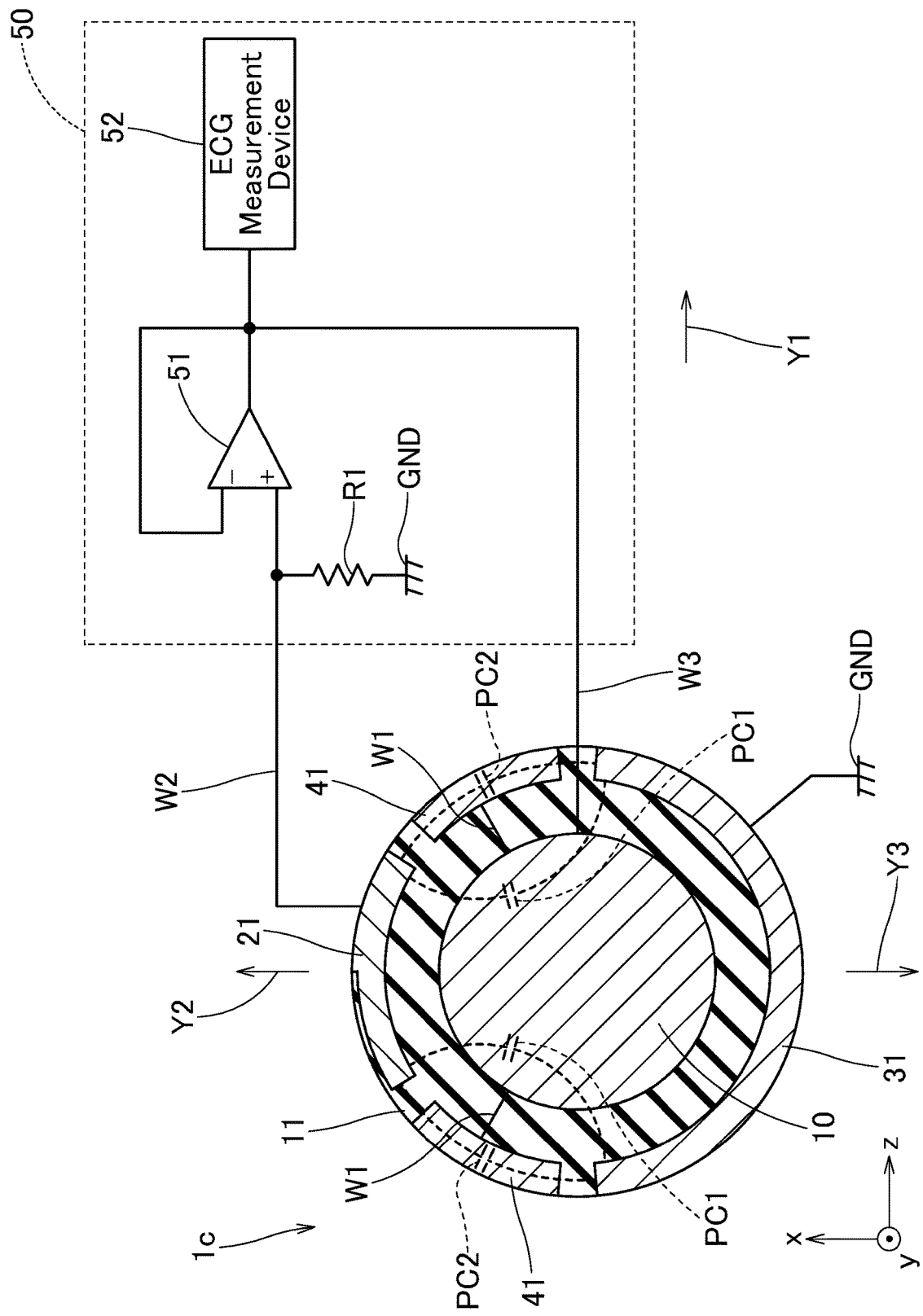
FIG. 8 is a cross-sectional view of a steering wheel 1c in accordance with a fourth embodiment.

FIG. 8 is a cross-sectional view of a rim of a steering wheel (i.e. grip) 1c in accordance with the fourth embodiment. Members with common reference numerals with the steering wheel 1 of the first embodiment have the same configurations as the first embodiment, therefore detailed descriptions of those members will be omitted. Compared with the steering wheel 1 of FIG. 2, in the steering wheel 1c shown in FIG. 8, a part of the surface of the sensing electrode 21 is covered by the cladding layer 11.

While a few exemplary embodiments have been described in detail above, those are illustrative only, and the scope of the claims should not be limited thereby. The art described in the claims includes modifications and variations of the exemplary embodiments presented above. Each of the technical elements illustrated in the present specification and the drawings may exert a technical effect alone or in various combinations, and the combinations of the technical elements should not be limited to those originally claimed. The art illustrated in the present specification and the drawings may concurrently achieve a plurality of objectives, while it has a technical significance if it achieves any one of such objectives.

Modifications

Although the steering wheel has been described above as an example of the grip, application of the present art should not be limited thereby. The art of the present specification can be applied to any grip that includes a core and is shaped for gripping by a man. By way of example, the art of the present specification can be applied to grips of a handlebar of a motorcycle or a bicycle, a grip(s) of a control yoke of an aircraft, which are not annular in shape. The art may further be applied to a grip of devices other than a steering device such as a grip of a health appliance (e.g. a body fat scale).

An insulating layer or a resistive layer may be disposed over a portion of the surface of the sensing electrode, as in the steering wheel 1c shown in FIG. 8. Here, the resistive layer is intended to refer to a layer that has an intermediary resistive value between an insulating layer and a conductive layer. Particularly, in the steering wheel 1c shown in FIG. 8, the cladding layer 11 covers a part of the surface of the sensing electrode 21. Such a configuration will help improve the design and/or touch of the steering wheel. In order to limit an elevation of the impedance $Z_b$ explained above to an acceptable level, the insulating layer or resistive layer may be thinned, or the area and/or the position the sensing electrode is covered may be adjusted.

Material of the sensing electrode 21, ground electrode 31 and shield electrode 41 should not be limited to metal. Any materials having electrical conductivity can be a material for those electrodes.

The sensing electrode 21, ground electrode 31 and shield electrode 41 may all be formed from metal. The metal electrodes will add an accent to the design of the steering wheel and improve the design of the steering wheel.

In the steering wheel 1 of the first embodiment shown in FIG. 2, the shield electrodes 41 are exposed on the surface of the steering wheel. However, the configuration of the shield electrode 41 should not be limited thereby. The shield electrode 41 is able to suppress the parasitic capacitance PC2 described above as long as it is located in proximity to the surface of the steering wheel. Therefore, the shield electrode 41 may be embedded in the cladding layer 11.

Application of the art of the present specification should not be limited to electrodes for acquiring an electrocardiogram. The art of the present specification may also be applied to electrodes for acquiring such a signal as body temperature, blood pressure or the like.

The arrangements of the sensing electrode 21, ground electrode 31 and shield electrodes 41 illustrated in the foregoing embodiments are mere examples.

The steering wheel is only an example of the grip. The body ground GND is only an example of a reference voltage portion.

What is claimed is:

1. A grip comprising:
   a core that has electrical conductivity, the core being disposed inside the grip for forming a structure of the grip;
   a sensing electrode for detecting a biological signal of a user, the sensing electrode being exposed on a surface of the grip, and being connected with the core via a voltage follower circuit; and
   a ground electrode that is connected with a reference voltage portion,
   wherein:
   the core, the sensing electrode and the ground electrode are insulated from one another; and
   the ground electrode is located at such a position that the core is able to reduce a parasitic capacitance which exists between the ground electrode and the sensing electrode.

2. The grip of claim 1, wherein, in a cross-sectional surface of the grip:
   the core is located in proximity to a center of the cross-sectional surface;
   the sensing electrode is located in a vicinity of an outer circumference of the cross-sectional surface; and
   the ground electrode is located separate from the sensing electrode in a vicinity of the outer circumference of the cross-sectional surface.

3. The grip of claim 2 further comprising at least one shield electrode that is located between the sensing electrode and the ground electrode in a vicinity of the outer circumference of the cross-sectional surface, the shield electrode being electrically connected with the core.

4. The grip of claim 3, wherein the shield electrode is exposed on the surface of the grip.

5. The grip of claim 3, wherein the shield electrode is covered with an insulating layer or a resistive layer on a surface thereof.

6. The grip of claim 1, wherein the ground electrode is exposed on the surface of the grip.

7. The grip of claim 1, wherein the ground electrode is covered with an insulating layer or a resistive layer on a surface thereof.

8. The grip of claim 1, wherein:
   the voltage follower circuit includes an operational amplifier;

an inverting input terminal and an output terminal of the operational amplifier are connected with one another;

the sensing electrode and the reference voltage portion are each connected with a non-inverting input terminal of the operational amplifier; and the output terminal is connected with the core.

9. The grip of claim 1, wherein an insulating layer or a resistive layer covers a part of a surface of the sensing electrode.

10. The grip of claim 1, wherein:

the grip is a steering wheel for a vehicle; and the sensing electrode and the ground electrode are provided for both a left hand and a right hand of a driver.

11. The grip of claim 10, wherein the sensing electrodes are configured to detect an electrocardiogram of the driver.

* * * * *